United States Patent [19]

Wolters et al.

[11] Patent Number: 5,681,957

[45] Date of Patent: Oct. 28, 1997

[54] PROCESS FOR THE PREPARATION OF SUBSTITUTED 2-FLUORO-PYRIMIDINES

[75] Inventors: Erich Wolters, Köln; Guido Steffan, Odenthal; Alexander Klausener, Köln, all of Germany

[73] Assignee: Bayer Aktiengesellschaft, Leverkusen, Germany

[21] Appl. No.: 643,214

[22] Filed: May 3, 1996

[30] Foreign Application Priority Data

May 11, 1995 [DE] Germany ............... 195 17 186.1

[51] Int. Cl.⁶ .............. C07D 239/02; C07D 413/04; C07D 403/04

[52] U.S. Cl. ............. 544/334; 544/122; 544/180; 544/217; 544/295; 544/296; 544/319; 544/320; 544/321; 544/326; 544/328; 544/329; 544/333; 544/335

[58] Field of Search ................ 544/295, 296, 544/319, 320, 321, 326, 328, 329, 333, 334, 335, 122, 180, 217

[56] References Cited

U.S. PATENT DOCUMENTS

| | | | |
|---|---|---|---|
| 4,226,995 | 10/1980 | Demosthene et al. | 544/334 |
| 5,266,697 | 11/1993 | Escher et al. | 544/320 |
| 5,378,845 | 1/1995 | Escher et al. | 544/319 |

FOREIGN PATENT DOCUMENTS

| | | |
|---|---|---|
| 0006062 | 12/1979 | European Pat. Off. . |
| 0514551 | 11/1992 | European Pat. Off. . |
| 0547411 | 6/1993 | European Pat. Off. . |
| 0582288 | 2/1994 | European Pat. Off. . |

OTHER PUBLICATIONS

Chemical Abstracts, vol. 83, abstract No. 131545t, p. 504, (1975).
D.J. Brown, et al., J. Chem. Soc., Perkin II, pp. 204–208, (1974).
J.A. Bee, et al., J. Chem. Soc. (C), pp. 2031–2037, (1966).
Derwent Abstracts, abstract of JP 03-193,766, (1991).
Krchnak et al., Diazotisation of the Amino Group on the Pyrimidine Nucleus, Collection Czechoslov. Chem. Commun., vol. 40, pp. 1390–1395 1975.

*Primary Examiner*—Mukund J. Shah
*Assistant Examiner*—Brenda Coleman
*Attorney, Agent, or Firm*—Sprung Kramer Schaefer & Briscoe

[57] ABSTRACT

Unsubstituted or substituted 2-fluoro-pyrimidines can be prepared by reaction of the underlying 2-amino-pyrimidines with diazotization agents, mixtures of HF and $H_2O$ containing 30–70% by weight of HF, based on the total of HF and $H_2O$, serving as reaction medium. The reaction medium can also contain diluents and/or inorganic salts, preferably fluorides.

10 Claims, No Drawings

PROCESS FOR THE PREPARATION OF SUBSTITUTED 2-FLUORO-PYRIMIDINES

The invention relates to a novel process for the preparation of 2-fluoro-pyrimidines by reaction of 2-amino-pyrimidines with a diazotization agent in hydrogen fluoride/water mixtures.

Substituted 2-fluoro-pyrimidines are important starting compounds, for example for the preparation of pharmaceutical and agrochemical active compounds, and dye-stuffs. Those which may be mentioned by way of example are herbicidal active compounds, as are described, for example, in Patent Applications EP 581 960, EP 514 551 or EP 547 411.

Substituted 2-halogeno-pyrimidines may be generally prepared in the following ways:

1. By diazotization of correspondingly substituted 2-amino-pyrimidines with an inorganic nitrite, such as sodium nitrite, and subsequent hydrolysis with concentrated hydrohalic acid, analogously to a process described in J. Chem. Soc., C, 1966, 2031. A great disadvantage of this process is that, in this case, only highly unsatisfactory yields are obtained. Thus, for example, 2-chloro-4,6-dimethoxypyrimidine, of interest as starting compound for the preparation of herbicidal active compounds, can only be obtained in 29% yield. Similarly poor results are described in JP 03 193 766. The preparation of 2-fluoro-4,6-dimethyl-pyrimidine from the corresponding 2-amino-pyrimidine only succeeds in a 26% yield (J. Chem. Soc., Perkin II, 204 (1974)). The preparation of 2-fluoro-4,6-dimethoxy-pyrimidine which is of particular interest in synthesis because of its increased reactivity in comparison with the said 2-chloro-4,6-dimethoxy-pyrimidine by diazotization of 2-amino-4,6-dimethoxy-pyrimidine is not described in the literature at all.

2. By reaction of correspondingly substituted propane diimidate or salts thereof with cyanamide in the presence of a base and subsequent cyclization in the presence of hydrogen halide (EP 582 288) of the correspondingly substituted cyanoimidate thus obtained. In this manner, 2-chloro-4,6-dimethoxy-pyrimidine is accessible in a moderate yield. The yields in the case of 2-bromo-4,6-dimethoxy-pyrimidine when this process is used are very small, and the analogous preparation of 2-fluoro-4,6-dimethoxy-pyrimidine is not described.

Quite generally, the preparation of unsubstituted or substituted 2-halogeno-pyrimidines, and amongst them, in particular, the preparation of substituted 2-fluoro-pyrimidines, poses a particularly difficult preparative problem, as the generally low yields described in the literature verify. This applies especially, if the published literature is followed, to the synthesis of 2-fluoro-4,6-dialkyl-, 2-fluoro-4-alkoxy- and 2-fluoro-4,6-dialkoxy-pyrimidines, each of which may optionally be substituted in the alkyl moiety.

The object therefore was still to develop a process which may be carried out industrially and gives satisfactory reaction yields for the preparation of substituted 2-fluoro-pyrimidines, in particular 2-fluoro-4,6-dialkyl-, 2-fluoro-4-alkoxy- and 2-fluoro-4,6-dialkoxy-pyrimidines substituted in the alkyl moiety, which satisfies both economic and ecological demands.

This object is achieved by the process of the invention.

The invention relates to a process for the preparation of 2-fluoro-pyrimidines of the formula

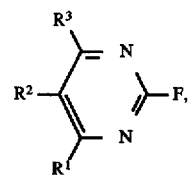

in which $R^1$, $R^2$ and $R^3$, independently of each other, denote hydrogen, unsubstituted or substituted $C_1$–$C_6$-alkyl, $C_3$–$C_8$-cycloalkyl, unsubstituted or substituted aryl or heterocyclyl, halogen, unsubstituted or substituted $C_1$–$C_6$-alkoxy, $C_1$–$C_6$-alkoxycarbonyl, $C_1$–$C_6$-alkylcarbonyloxy, cyano, di-$C_1$–$C_6$-alkylamino or the group —$SO_n$—$R^4$, in which n represents 0, 1 or 2 and $R^4$ represents unsubstituted or substituted $C_1$–$C_6$-alkyl, unsubstituted or substituted $C_1$–$C_6$-alkoxy, unsubstituted or substituted aryl, unsubstituted or substituted aryloxy or unsubstituted or substituted arylthio, which is characterized in that 2-amino-pyrimidines of the formula

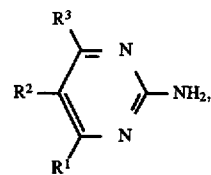

in which the substituents $R^1$, $R^2$, $R^3$ and $R^4$ have the meaning given above, are reacted with a diazotization agent at −60° to +40° C. in mixtures of HF and $H_2O$ containing 30 to 70% by weight of HF, based on the total of HF and $H_2O$, in the presence or absence of a diluent and in the presence or absence of one or more salt-like compounds.

Alkyl represents straight-chain or branched alkyl having 1 to 6 carbon atoms which may optionally be substituted by halogen, $C_1$–$C_4$-alkoxy, $C_1$–$C_4$-alkylthio, halo-$C_1$–$C_4$-alkoxy or halo-$C_1$–$C_4$-alkylthio, preferably for alkyl having 1 to 4 carbon atoms which may optionally be substituted by halogen, and particularly preferably, for methyl which may optionally be substituted by halogen. Those which may be mentioned in particular are methyl, difluoromethyl and trifluoromethyl.

Cycloalkyl represents saturated cycloalkyl having 3 to 8 chain members which may optionally be substituted by up to 3 $C_1$–$C_4$-alkyl or halogen, preferably alkyl-substituted cycloalkyl having 3 to 6 chain members, and particularly preferably, cycloalkyl having 3 to 6 chain members. Those which may be mentioned in particular are cyclopropyl and cyclopentyl.

Unsubstituted or substituted aryl, aryloxy and arylthio generally represent oxygen- or sulphur-linked phenyl optionally having 0 to 5 further substituents, preferably 0 to 3 further substituents, and particularly preferably 0 or 1 further substituent, the substituents originating from the group consisting of the unsubstituted or substituted $C_1$–$C_6$-alkyl groups, halogen, unsubstituted or substituted $C_1$–$C_6$-alkoxy, $C_1$–$C_6$-alkoxycarbonyl or cyano, preferably from the group consisting of the unsubstituted or substituted $C_1$–$C_4$-alkyl groups, halogen, $C_1$–$C_4$-alkoxy or $C_1$–$C_4$-alkoxycarbonyl, and particularly preferably from the group consisting of the alkyl groups and halogen, and can be arranged in the ortho, meta or para position to one another.

Unsubstituted or substituted heterocyclyl represents mononuclear unsubstituted or substituted saturated, unsaturated or aromatic heterocyclyl selected from the group consisting of 4- to 6-membered heterocycles having 1 to 3 heteroatoms within the ring system, and preferably unsubstituted or substituted saturated, unsaturated or aromatic heterocyclyl selected from the group consisting of the 5- to 6-membered heterocycles having 1 to 3 heteroatoms within the ring system, suitable substituents being alkyl having 1 to 4 carbon atoms, haloalkyl or halogen, preferably alkyl having 1 to 3 carbon atoms, trifluoromethyl and fluorine or chlorine, and the said substituents being able to adopt in principle any positions within the heterocyclic system. Those which may be mentioned in particular are 1-, 2- and 3-pyridinyl, 2-, 4- and 5-pyrimidinyl, 2- and 3-furyl, 2- and 3-thiophenyl, 2-, 4- and 5-thiazolyl, 2-, 4- and 5-oxazolyl, 1-pyrrolyl, 1- and 2-imidazolyl, 1-triazolyl, piperidinyl, morpholinyl, 4-[2,6-dimethyl-morpholinyl], 4-(N-methyl-piperazinyl], pyrrolidinyl and 2- and 3-oxetanyl.

Halogen represents fluorine, chlorine, bromine and iodine, preferably fluorine, chlorine and bromine, and particularly preferably chlorine.

Unsubstituted or substituted alkoxy represents alkoxy having 1 to 6 carbon atoms, preferably 1 to 4 carbon atoms, in the alkyl moiety, which may optionally be substituted by halogen or a further $C_1$–$C_4$-alkoxy, halogen preferably representing fluorine and further alkoxy preferably representing methoxy.

Unsubstituted or substituted alkoxycarbonyl or alkylcarbonyloxy has 1 to 6 carbon atoms, preferably 1 to 4 carbon atoms, in the alkyl moiety and particularly preferably represents methoxycarbonyl and ethoxycarbonyl.

Dialkylamino represents dialkylamino containing identical or different alkyl groups having 1 to 6, preferably 1 to 4, carbon atoms.

Preferably, the 2-amino-pyrimidines of the formula

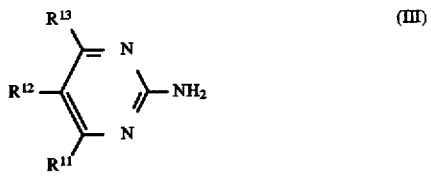

(III)

are used, in which $R^{11}$, $R^{12}$ and $R^{13}$ independently of each other, denote hydrogen, unsubstituted or substituted $C_1$–$C_6$-alkyl, $C_3$–$C_6$-cycloalkyl, unsubstituted or substituted aryl or heterocyclyl or unsubstituted or substituted $C_1$–$C_6$-alkoxy.

Particularly preferably, 2-amino-pyrimidines of the formula

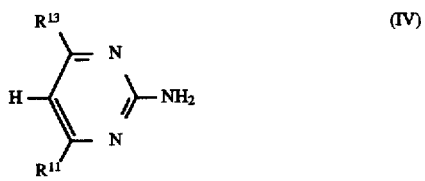

(IV)

are used, in which $R^{11}$ and $R^{13}$, independently of each other, denote hydrogen, unsubstituted or substituted $C_1$–$C_6$-alkyl, $C_3$–$C_6$-cycloalkyl, unsubstituted or substituted aryl or heterocyclyl or unsubstituted or substituted $C_1$–$C_6$-alkoxy.

Very particularly preferably, 2-amino-pyrimidines of the formula

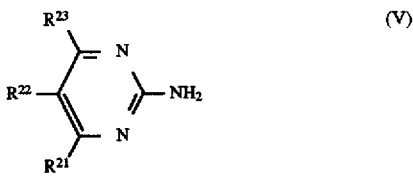

(V)

are used, in which, of the radicals $R^{21}$, $R^{22}$ and $R^{23}$, one or two, preferably $R^{22}$, represent hydrogen and the remaining radicals, independently of each other, denote methyl, ethyl, methoxy, ethoxy, monofluorinated to trifluorinated methyl, monofluorinated to pentafluorinated ethyl, monofluorinated to trifluorinated methoxy or monofluorinated to pentafluorinated ethoxy.

In particular, under the compounds of the formulae (II) to (V), the compounds listed in Table 1 may be mentioned:

TABLE 1

Compounds which are particularly easily accessible on the routes of the process according to the invention

| $R^1$ | $R^2$ | $R^3$ |
|---|---|---|
| $CH_3$ | H | H |
| $OCH_3$ | H | H |
| $CF_3$ | H | H |
| $OCF_3$ | H | H |
| $OCHF_2$ | H | H |
| $CH_3$ | H | $CH_3$ |
| $OCH_3$ | H | $CH_3$ |
| $CF_3$ | H | $CH_3$ |
| $OCF_3$ | H | $CH_3$ |
| $OCHF_2$ | H | $CH_3$ |
| $OCH_3$ | H | $OCH_3$ |
| $CF_3$ | H | $OCH_3$ |
| $OCF_3$ | H | $OCH_3$ |
| $OCHF_2$ | H | $OCH_3$ |
| $CF_3$ | H | $CF_3$ |
| $OCF_3$ | H | $CF_3$ |
| $OCHF_2$ | H | $CF_3$ |
| $OCF_3$ | H | $OCF_3$ |
| $OCHF_2$ | H | $OCF_3$ |
| $OCHF_2$ | H | $OCHF_2$ |
| H | $OCH_3$ | H |

The procedure of the process of the invention is characterized in that the said 2-amino-pyrimidines are introduced in a mixture of hydrogen fluoride, water, optionally one or more further organic solvents stable under the reaction conditions as diluent, and optionally one or more inorganic salts, preferably inorganic fluorides, a diazotization agent of the formula $$ANO_2 \quad (VI)$$

in which

A represents a metal ion from the group consisting of the alkali metals, or ammonium or straight-chain or branched alkyl having 1 to 6 carbon atoms, preferably a metal from the group consisting of the alkali metals, and particularly preferably sodium or potassium, is introduced into this mixture, preferably in dissolved form, and the reaction product, after the reaction is completed, is worked up in a manner known per se.

The substituted 2-amino-pyrimidines used as starting material are accessible, for example, by a process described in EP 424 849.

The process of the invention is carried out in a reaction mixture of hydrogen fluoride and water which, based on the total amount of HF and $H_2O$, has an HF content of 30 to 70% by weight, preferably of 40 to 70% by weight, and to which are optionally added inorganic salts, preferably inorganic fluorides, very particularly preferably potassium hydrogen fluoride ($KHF_2$), more precisely in such a manner that, based on the total reaction mixture, a content between 0% by weight and the saturation concentration of this inorganic salt or these inorganic salts is given.

In an individual case, it can be expedient to admix to this solvate system one or more further organic solvents for dilution. Those which may be mentioned by way of example are ethers, aromatic or aliphatic hydrocarbons, halogenated solvents or other solvents stable under the reaction conditions. It is perfectly possible to carry out the said reaction as a two-phase reaction. This is generally the case if the diluent used separates in view of relatively large water contents within the hydrogen fluoride used. Preferably, no solvent is employed.

The process of the invention is generally carried out within a temperature range of +40° to −60° C, preferably from +25° to −40° C., particularly preferably from +20° to −20° C., very particularly preferably from +15° to −20° C.

The pressure is not critical for the process of the invention. Generally, the process of the invention is carried out in a pressure range from 0.5 to 1.5 bar, preferably at atmospheric pressure conditions. However, it is also possible to carry out the reaction under reduced pressure or under elevated pressure.

Generally, it is expedient to introduce the said nitrites of the general formula (VI), if these are inorganic substances, in solution, preferably in aqueous solution. However, it is also possible in principle to introduce the said nitrites into the reaction mixture in undissolved form.

If organic nitrites of the formula (VI) are used, these can be introduced in pure form, e.g. as gaseous methyl nitrite or as liquid isoamyl nitrite, but, optionally, alternatively in dilute form, such as in the case of gaseous methyl nitrite diluted with inert gases such as nitrogen, carbon dioxide or argon or, in the case of liquid alkyl nitrites such as isoamyl nitrite, diluted with suitable organic solvents stable under the reaction conditions.

Generally, stoichiometrically equivalent amounts of the diazotization agent are used, based on the unsubstituted or substituted 2-amino-pyrimidine used. However, in an individual case, it can also be expedient to use the diazotization agent in deficiency or excess, for instance in the range from 0.5 to 3-fold, preferably 0.9 to 2-fold, particularly preferably 1.1 to 1.8-fold, based on the molar amount of the substituted 2-amino-pyrimidine used.

In the case where the process of the invention is carried out under homogeneous reaction conditions, comparatively short reaction times are observed.

In the case where the process of the invention is carried out under two-phase conditions, the reaction duration can be somewhat longer. In this case, it can occasionally be of great advantage to ensure vigorous mixing of the reaction mixture by using suitable stirring units.

It is characteristic of the process of the invention and extremely surprising that when highly defined ratios of hydrogen fluoride and water are used, particularly high reaction yields are found. Whereas only very low reaction yields of, e.g. 2-fluoro-4,6-dialkoxy-pyrimidines were obtained, for example, in a solvate system which contains hydrogen fluoride and water in a weight ratio of 20 to 80 and which has additionally been saturated with potassium hydrogen fluoride, use of a solvate system of hydrogen fluoride and water having a weight ratio of 40 to 60 under otherwise identical reaction conditions resulted in reaction yields which were generally above approximately 40% of theory and, when a weight ratio of 65 to 35 was used, reaction yields were even found which were often above approximately 70% of theory. However, if a solvate system was used in which hydrogen fluoride and water were present in a ratio of more than 75 to 25, again, markedly lower reaction yields were observed with considerably prolonged reaction times or incomplete conversions.

This concentration-dependent reaction course, based on the composition of the solvate system, which is expressed in different reaction times and reaction yields, is surprising and could not be taken from the literature in the form observed. Furthermore, it is surprising that, within this empirically found optimal concentration range, not only is a considerable acceleration of the reactions in question observed, but also that the isolated reaction products have a considerably higher content and may be isolated considerably more easily from the reaction mixture.

The process of the invention is advantageously carried out for economic reasons in such a manner that as high a concentration as possible of substrate in the solvate system is present, if this does not impair yields and selectivities in an unreasonable manner. The substrate concentration in the solvate system used which is optimum in this sense can vary within broad limits and is essentially determined by the properties of the substrate itself, by the organic solvent optionally additionally used and by the inorganic salts optionally additionally dissolved in the solvate system.

The optimum concentration is generally between about 5% by weight and 65% by weight, preferably between about 10% by weight and 50% by weight, and particularly preferably between about 10% by weight and 40% by weight, based on the total amount by weight of the components hydrogen fluoride and water contained in the solvate system.

The amount of the organic solvent(s) optionally additionally used can likewise be varied within broad limits. It can be, for example, between 0% by volume and 95% by volume, based on the total volume of the remaining reaction mixture.

The desired substituted 2-fluoro-pyrimidines of the general formula (I) are isolated by a process known in principle. However, it is characteristic of the process of the invention that particularly clean reaction products are obtained by the crude product mixtures first being diluted to a hydrogen fluoride content of 10% to 40% by weight in one or more steps, the majority of the reaction product 2-fluoro-pyrimidine formed generally precipitating in crystalline form and being able to be readily separated off. Further amounts of the product formed can be produced by reextracting the aqueous mixture with suitable organic extractants, e.g. chlorinated hydrocarbons. Alternatively, the entire reaction mixture may also be worked up by extraction in a manner conventional per se, the crude reaction products obtained after removing the extractant being purifiable, for example, by distillation, recrystallization or sublimation.

If the reaction is carried out in the presence of a suitable organic solvent, as early as the dilution stage, the product is extracted into the organic phase. After drying and separating off the organic solvent and after filtering off by suction the reaction product precipitated out in the crystalline state, the target compound can be further purified, if necessary, by conventional purification processes, such as by distillation, crystallization or sublimation.

Examples

Example 1

70.2 g (0.452 mol) of 2-amino-4,6-dimethoxypyrimidine in 450 ml of 65% strength aqueous hydrofluoric acid were introduced into a 1.5 litre Teflon vessel which was equipped with stirrer, internal thermometer, dropping funnel and gas discharge tube with gas meter. At a temperature of −10° C., 93.2 g of a 50% strength aqueous potassium nitrite solution (0.547 mol) were added dropwise in the course of 2.4 hours. During the dropwise addition of the potassium nitrite solution, nitrogen evolved vigorously. The total amount of nitrogen evolved was approximately 10 l. Then, with stirring at 0° C., 300 ml of methylene chloride and then 300 ml of water were added to the reaction mixture. The organic phase was separated off, dried with sodium sulphate and concentrated. 52.0 g of a white crystalline mass were obtained which, according to GC, $^1$H-NMR and MS, comprised 98.6% 2-fluoro-4,6-dimethoxypyrimidine. This corresponds to a yield of 71.7% of the theoretical yield. The product can be recrystallized from hexane or sublimed and then arises in long white needles.

F.p.: 89°–90° C.

MS: M$^+$=158

$^1$H-NMR(CDCl$_3$): 5.95 (d; J$_{5,F}$=2.67; 5-H) ppm 3.95 (s; (CH$_3$)$_2$) ppm

Example 2

70.2 g (0.452 mol) of 2-amino-4,6-dimethoxypyrimidine in 450 ml of 40% strength aqueous hydrofluoric acid were introduced into a 1.5 litre Teflon vessel which was equipped with stirrer, internal thermometer, dropping funnel and gas discharge tube with gas meter. At a temperature of −10° C., 93.2 g of a 50% strength aqueous potassium nitrite solution (0.547 mol) were added dropwise in the course of 3 hours. During the dropwise addition of the potassium nitrite solution, nitrogen evolved vigorously. The total amount of nitrogen evolved was approximately 10 l. The violet-tinted product precipitated out was filtered off by suction, taken up into 200 ml of methylene chloride, dried using sodium sulphate and concentrated. 29.2 g of a violet-tinted crystalline mass were obtained, which comprised, according to GC, 99.0% 2-fluoro-4,6-dimethoxypyrimidine. This corresponds to a yield of 41% of theoretical yield. The aqueous phase was extracted five times, each time with 50 ml of methylene chloride, the organic phase was dried using sodium sulphate and concentrated. 3.5 g of a dark violet crystalline mass were obtained, which comprised, according to GC, 73.4% 2-fluoro-4,6-dimethoxypyrimidine. This corresponds to an additional yield of 3.6% of the theoretical yield.

Example 3

70.2 g (0.452 mol) of 2-amino-4,6-dimethoxypyrimidine in 450 ml of 65% strength aqueous hydrofluoric acid and 80.1 g (1.025 mol) of potassium hydrogen fluoride were introduced into a 1.5 litre Teflon vessel which was equipped with stirrer, internal thermometer, dropping funnel and gas discharge tube with gas meter. At a temperature of −10° C., 93.2 g of a 50% strength aqueous potassium nitrite solution (0.547 mol) were added dropwise in the course of 2.4 hours. During the dropwise addition of the potassium nitrite solution, nitrogen evolved vigorously. The total amount of nitrogen evolved was approximately 10 l. Then, with stirring at 0° C., 300 ml of methylene chloride and then 300 ml of water were added to the reaction mixture. The organic phase was separated off, dried with sodium sulphate and concentrated. 53.6 g of a white crystalline mass were obtained which, according to GC, comprised 98.9% 2-fluoro-4,6-dimethoxy-pyrimidine. This corresponds to a yield of 74.1% of the theoretical yield.

Comparison example 1

70.2 g (0.452 mol) of 2-amino-4,6-dimethoxypyrimidine in 450 ml of 75% strength aqueous hydrofluoric acid were introduced into a 1.5 litre Teflon vessel which was equipped with stirrer, internal thermometer, dropping funnel and gas discharge tube with gas meter. At a temperature of −10° C., 93.2 g of a 50% strength aqueous potassium nitrite solution (0.547 mol) were added dropwise in the course of 3.2 hours. During the dropwise addition of the potassium nitrite solution, only slight nitrogen evolution occurred. The total amount of nitrogen evolved was only approximately 1.2 l. Then, with stirring at 0° C., 300 ml of methylene chloride were added to the reaction mixture. The organic phase was separated off, dried using sodium sulphate and concentrated. 3.5 g of a white crystalline mass were obtained which, according to GC, comprised 98.7% 2-fluoro-4,6-dimethoxypyrimidine. This corresponds to a yield of 4.8% of the theoretical yield.

Comparison Example 2

70.2 g (0.452 mol) of 2-amino-4,6-dimethoxypyrimidine in 450 ml of 20% strength aqueous hydrofluoric acid were introduced into a 1.5 litre Teflon vessel which was equipped with stirrer, internal thermometer, dropping funnel and gas discharge tube with gas meter. At a temperature of −10° C., 93.2 g of a 50% strength aqueous potassium nitrite solution (0.547 mol) were added dropwise in the course of 4.5 hours. During the dropwise addition of the potassium nitrite solution, only a very slight nitrogen evolution occurred. The total amount of nitrogen evolved was less than 1 l. The blue product precipitated out, which was poorly soluble in methylene chloride, was filtered off by suction, washed with 200 ml of water and dried in the drying cabinet 41.4 g of a blue crystalline mass were obtained, which comprised approximately 10% by weight 2-fluoro-4,6-dimethoxypyrimidine. This corresponds to a yield of approximately 5.7% of the theoretical yield.

Examples 4–10

In the same manner as described in Example 3, the compounds listed in Table 2 were prepared from the corresponding 2-amino-pyrimidines.

TABLE 2

| Reaction product | Yield [%] | $^1$H-NMR (CDCl$_3$) | F.p. [°C.] | b.p. [°C./mb] |
|---|---|---|---|---|
| 2-fluoro-pyrimidine | 34.1 | 8.7 ppm, (m), 2H<br>7.3 ppm, (m), 1H | | |
| 2-fluoro-4,6-dichloro-pyrimidine | 72.4 | 7.2 ppm, (d) | 38–39 | |
| 2-fluoro-5-bromo-pyrimidine | 76.7 | 8.7 mmp (d) | 102 | |
| 2-fluoro-4-methyl-pyrimidine | 44.1 | 8.5 ppm, (m), 1H<br>7.1 ppm, (m), 1H<br>2.6 ppm, (s), 3H | | |
| 2-fluoro-4,6-dimethyl-pyrimidine | 28.4 | 7.0 ppm, (d), 1H<br>2.5 ppm, (s), 6H | | |
| 2-fluoro-4-methoxy-6-methylpyrimidine | 45.8 | 6.5 ppm, (d), 1H<br>4.0 ppm, (s), 3H<br>2.4 ppm, (s), 3H | 25 | 80/35 |

What is claimed is:

1. A process for the preparation of a 2-fluoro-pyrimidine of the formula

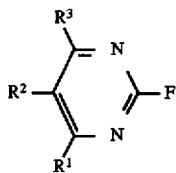

in which
one or two of $R^1$, $R^2$ and $R^3$ represent hydrogen and the remainder, independently of each other, denote unsubstituted or substituted $C_1$–$C_6$-alkyl, $C_3$–$C_8$-cycloalkyl, unsubstituted or substituted phenyl or heterocyclyl, halogen, unsubstituted or substituted $C_1$–$C_6$-alkoxy, $C_1$–$C_6$-alkoxycarbonyl, $C_1$–$C_6$-alkylcarbonyloxy, cyano, di-$C_1$–$C_6$-alkylamino or the group-$So_n$-$R^4$, in which n represents 0, 1 or 2 and $R^4$ represents unsubstituted or substituted $C_1$–$C_6$-alkyl, unsubstituted or substituted $C_1$–$C_6$-alkoxy, unsubstituted or substituted phenyl, unsubstituted or substituted aryloxy or unsubstituted or substituted arylthio, in which a 2-amino-pyrimidine of the formula

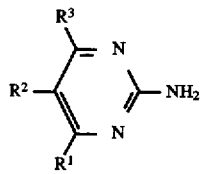

in which the substituents $R^1$, $R^2$, $R^3$ and $R^4$ have the meaning given above, is reacted with a diazotization agent at −60° to +40° C. in a mixture of HF and $H_2O$ containing 30 to 70% by weight of HF, based on the total of HF and $H_2O$ whereby the concentration of substrate in the solvate system is 5 to 65% by weight, based on the total amount by weight of the compounds hydrogen fluoride and water contained in the solvate system and wherein "unsubstituted or substituted heterocyclyl" means mononuclear unsubstituted or substituted saturated, unsaturated or aromatic heterocyclyl selected from the group consisting of 4- to 6-membered heterocycles having 1 to 3 heteroatoms within the ring system, the substituents being alkyl having 1 to 4 carbon atoms, haloalkyl or halogen, and being able to adopt any positions within the heterocyclic system.

2. The process of claim 1, which is carried out in the presence of diluent.

3. The process of claim 1, which is carried out in the presence of one or more inorganic fluorides.

4. The process of claim 1, in which a 2-amino-pyrimidine of the formula

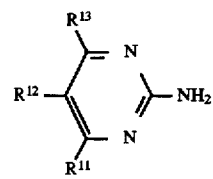

is used, in which
one or two of $R^{11}$, $R^{12}$ and $R^{13}$ represent hydrogen and the remainder, independently of each other, denote unsubstituted or substituted $C_1$–$C_6$-alkyl, $C_3$–$C_6$-cycloalkyl, unsubstituted or substituted phenyl or heterocyclyl or unsubstituted or substituted $C_1$–$C_6$-alkoxy.

5. The process of claim 1, in which a 2-amino-pyrimidine of the formula

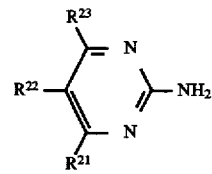

is used, in which, of the radicals
$R^{21}$, $R^{22}$ and $R^{23}$, one or two represent hydrogen and the remaining radicals, independently of each other, denote methyl, ethyl, methoxy, ethoxy, monofluorinated to trifluorinated methyl, monofluorinated to pentafluorinated ethyl, monofluorinated to trifluorinated methoxy or monofluorinated to pentafluorinated ethoxy.

6. The process of claim 1, in which the diazotization agent used is one of the formula $ANO_2$, in which
A represents a metal ion from the group consisting of the alkali metals, or ammonium or straight-chain or branched alkyl having 1 to 6 carbon atoms.

7. The process of claim 1, in which the diazotization agent is used in an amount in the range from 0.5-fold to three-fold, based on the molar amount of 2-amino-pyrimidine.

8. The process of claim 1, in which the product mixture is diluted to an HF content of 10–40% by weight and 2-fluoro-pyrimidine which crystallizes out is separated off.

9. The process of claim 8, wherein, after the crystallized 2-fluoro-pyrimidine has been separated off, the remaining reaction mixture is extracted with an organic solvent to recover additional amounts of 2-fluoro-pyrimidine.

10. The process of claim 9, which is carried out in the presence of a diluent, and the extraction is carried out simultaneously to the dilution of the exhaustively reacted reaction mixture to an HF content of 10–40% by weight.

* * * * *